United States Patent [19]

Pilgram

[11] 3,937,627

[45] Feb. 10, 1976

[54] PERCHLORYLPHENYLUREA HERBICIDE

[75] Inventor: Kurt H. G. Pilgram, Modesto, Calif.

[73] Assignee: Shell Oil Company, Houston, Tex.

[22] Filed: Feb. 19, 1975

[21] Appl. No.: 551,172

Related U.S. Application Data

[63] Continuation-in-part of Ser. No. 381,936, July 23, 1973, abandoned.

[52] U.S. Cl. ............................ 71/120; 260/453 R
[51] Int. Cl.$^2$ ......................................... A01N 9/20
[58] Field of Search ............... 71/120; 260/453 R X

[56] References Cited

UNITED STATES PATENTS

| | | | |
|---|---|---|---|
| 3,000,940 | 9/1961 | Raasch | 260/453 R |
| 3,254,984 | 6/1966 | Johnson | 71/120 |
| 3,278,292 | 10/1966 | Johnson | 71/120 |
| 3,681,422 | 8/1972 | Scherer et al. | 260/453 R |

Primary Examiner—Glennon H. Hollrah

[57] ABSTRACT

1-methoxy-1-methyl-3-(3-perchlorylphenyl)urea, having herbicidal activity.

4 Claims, No Drawings

PERCHLORYLPHENYLUREA HERBICIDE

This application is a continuation-in-part of application Ser. No. 381,936, filed July 23, 1973 now abandoned.

DESCRIPTION OF THE INVENTION 1-methoxy-1-methyl-3-(3-perchlorylphenyl)urea having the formula:

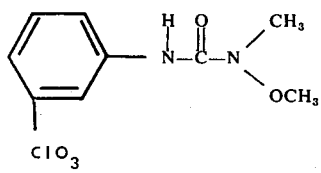

has been found to be a very active herbicide.

The herbicide of this invention can be prepared as follows:

a. Preparation of perchlorylbenzene (I)

225 grams (2.2 moles) of perchloryl fluoride gas was passed into a stirred suspension of 293 grams (2.2 moles) of aluminum trichloride in 4 liters of benzene at 10°–20°. The reaction was exothermic and the temperature was maintained within the desired limits by controlling the rate at which the fluoride was added and by cooling. By-product hydrogen chloride was removed as it formed. After about 3.5 hours, the amorphous aluminum salt was filtered from the reaction mixture. The filtrate was washed well with water, dried and the benzene was evaporated under reduced pressure (25 torr., 65°) in a dropping film rotary evaporator to give 258 grams (78% yield) of I, as a light yellow liquid.

b. Preparation of 1-nitro-3-perchlorylbenzene (II)

To a stirred mixture of 250 grams (1.56 moles) of I in 1.8 liters of concentrated sulfuric acid was gradually added a nitrating mixture of 175 grams (1.75 moles) of 63% nitric acid and 600 milliliters of concentrated sulfuric acid. The reaction mixture was maintained at 20°–30°. The mixture was stirred for 4 hours at room temperature, then poured over ice water and extracted with benzene several times. The combined benzene extracts were washed with water, dried and the benzene was removed using the dropping film rotary evaporator to give 280 grams (87% yield) of II as a brown-yellow oil.

c. Preparation of 3-perchlorylaniline hydrochloride (III)

To a stirred solution of 268 grams (1.3 moles) of II in 1.5 liters of ethanol and 1.5 liters of concentrated hydrochloric acid, 850 grams (4.5 moles) of stannous chloride was added in portions, the mixture being maintained at 50°–60° by heating. The mixture was held at 60° for 2 hours after the last of the stannous chloride had been added. The resulting mixture was concentrated under reduced pressure (25 torr., 75°–85°), then poured over ice and water and neutralized to a pH of 5–6 with sodium hydroxide solution. The resulting suspension was extracted repeatedly with ether. The combined ether extracts were dried, filtered and then treated with dry hydrogen chloride to give 95 grams (34% yield) of III, as a light-tan crystalline solid, melting with decomposition at 177°–178°.

d. Preparation of 3-perchlorylphenyl isocyanate (IV)

A slurry consisting of 43 grams (0.2 mole) of III and 39.6 grams (0.4 mole) of phosgene in 500 milliliters of benzene was gradually heated to reflux and refluxed for 3 hours. The resulting clear solution was concentrated under reduced pressure to give 38.7 grams (94.5% yield) of IV as a viscous brown liquid.

e. Preparation of 1-methoxy-1-methyl-3-(3-perchlorylphenyl)urea (V)

To a solution of 12.9 grams (0.064 mole) of IV in 250 milliliters of ether was added a solution of 4.9 grams (0.08 mole) of O,N-dimethylhydroxylamine in 350 milliliters of methanol. The resulting mixture was concentrated to dryness, washed with water and recrystallized from acetone/hexane (5:1) to give 11.8 grams (71% yield) of V as a white crystalline solid, melting point: 125°–126°. Its identity was confirmed by elemental analysis.

The compound of this invention has been found to be herbicidally effective with regard to a variety of plant species, including economically important species of grasses and broadleaved weeds. It has been found to be active both pre-emergence (applied to the soil prior to germination of the plat seeds) and post-emergence (applied to the foliage of the plant). It is particularly of interest as a pre-emergence herbicide.

Accordingly, herbicidal compositions of this invention comprise the urea of this invention and an inert agriculturally acceptable carrier therefor. Undesirable plant growth is destroyed or prevented by applying an effective amount of the urea, ordinarily in a herbicidal composition of one of the types described hereinafter to either the unwanted vegetation itself or to the area to be kept free of such unwanted vegetation.

The amount of the urea required for controlling unwanted plants will naturally depend upon the variety or varieties of plants involved, whether the urea is to be applied pre-emergence or post-emergence, the kind and condition of the soil (if applied pre-emergence), the degree of control desired, the character of the formulation used, the mode of application, the climate, the season of the year and other variables which must be and are taken into account by practioners of the art of chemical control of unwanted plants. Recommendation as to precise dosages are therefore not possible. In general, however, when applied pre-emergence to a locus to be protected, dosages of from about 0.1 to about 10 pounds per acre of the urea will be satisfactory. When applied post-emergence, the usual practice is to spray or dust the foliage of the plants to apply the needed dosage to the foliage. The nominal dosage in this case also is from about 0.1 to about 10 pounds per acre of the urea. Liquid and dust formulations for such application ordinarily contain from about ½ to 10 percent of the urea.

The urea may be formulated as a wettable powder, a dust, as granules, as a solution, an emulsifiable concentrate, an emulsion, suspension concentrate or aerosol. Wettable powders are usually compounded to contain from about 25 to about 75 percent by weight of toxicant and usually contain in addition to solid carrier, 3–10 percent by weight of a dispersing agent and, where necessary, up to 10 percent by weight of stabilizer(s) and/or other additives such as penetrants or stickers. Dusts are usually formulated as a concentrate having a similar composition to that of a wettable powder but without a dispersant, and are diluted in the field with further solid carrier to give a composition usually containing ½–10 percent by weight of toxicant. Generally, granules will contain ½–25 percent by weight toxicant and 0–10 percent by weight of additives such as stabilizers, slow release modifiers and binding agents. Any of the solid materials commonly used for formulating agricultural chemicals can be used. Examples include: talc, clays, pumice, diatomaceous earth, silica, walnut granules and flour, chalk and the like. Emulsifiable concentrates usually contain, in addition to the solvent and, when necessary, co-solvent, 10–50 percent weight per volume toxicant, 2–20 percent weight per volume emulsifiers and 0–20 percent per volume of appropriate additives such as stabilizers, penetrants and corrosion inhibitors. Suitable solvents include benzene, toluene, xylene, methanol, ethanol, acetone, methyl ethyl ketone, diethyl ketone, tetrahydrofuran, acetonitrile, dimethylformamide, dimethyl sulfoxide, sulfolane, sulfolene. Suspension concentrates are compounded so as to obtain a stable, non-sedimenting flowable product and usually contain 10–75 percent by weight of toxicant, 0.5–15 percent by weight of dispersing agents, 0.1–10 percent by weight of suspending agents such as protective colloids and thixotropic agents, 0–10 percent by weight of appropriate additives such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions of these formulations are obtained by diluting such wettable powders or concentrates with water. The said emulsions may be of the water-in-oil or of the oil-in-water type, and may have a thick mayonnaise-like consistency.

The compositions containing the urea may also contain other ingredients, for example, other compounds possessing pesticidal, especially insecticidal, acaricidal, herbicidal or fungicidal properties.

The pre-emergence hericidal activity of the urea of the invention was evaluated by planting seeds of watergrass and cress in test tubes, nominally measuring 25 × 200 millimeters, containing soil treated with the test compound at the rate of 0.1 and 1 milligrams of the active compound per tube designated in Table II as Rates I and II, respectively. The planted soil was held under controlled conditions of temperature, moisture, and light for 13 to 14 days. The amount of germination was then noted and the effectiveness of the test compound was rated on the basis of a 0 to 9 scale, 0 rating indicating no effect, 9 indicating death of the seedlings or no germination.

The post-emergence activity of the compound of this invention was evaluated by spraying 10-day old pigweed plants and 7-day old crabgrass plants to runoff with a liquid formulation of the test compound at the rates of 0.62 milliliters of an 0.04 percent solution designated Rate I in Table II, and 0.56 milliliters of an 0.5 percent solution designated Rate I in Table II. The sprayed plants were held under controlled conditions for 10 to 11 days and the effect of the test chemical was then evaluated visually, the results being rated on the 0 to 9 scale described above.

The results of the tests are summarized in Table I.

The herbicidal activity of the compound of this invention was determined with respect to several common species of weeds, by spraying a formulation of the test compound on to the soil in which the weed seeds had been planted (pre-emergence test) or on to the foliage of the plants (post-emergence tests). In each series of tests, the soil was held in containers that isolated that soil into a narrow band, or row. The solution of test chemical was sprayed over the band, from one end to the other, the concentration of the test compound in the formulation varying logarithmically from a higher value at one end of the band to a lower value at the other end of the band. The effect of the test chemical was evaluated visually and reported as the nominal rate of application, in pounds of test chemical per acre of the soil band, at which 90 percent inhibition of the growth of the weeds occurred, this being referred to as the 90 percent growth inhibition, or $GI_{90}$, dosage. Results of the pre-emergence tests, as well as the weed species involved, are set out in Table II, while similar data for the post-emergence tests are set out in Table III.

TABLE I

HERBICIDAL ACTIVITY

| Pre-emergence | | | | Post-emergence | | | |
| Watergrass | | Cress | | Crabgrass | | Pigweed | |
| Rate I | Rate II | Rate I | Rate II | Rate I | Rate II | Rate I | Rate II |
|---|---|---|---|---|---|---|---|
| 9 | 9 | 9 | 9 | 9 | 9 | 7 | 9 |

TABLE II

PRE-EMERGENCE TESTS
WEED SPECIES

| Ryegrass | Cheatgrass | Crabgrass | Watergrass | Pigweed | Mustard | Curly Dock | Seedling Quack grass | Green Foxtail | Lambs-quarter | Buckhorn Plantain |
|---|---|---|---|---|---|---|---|---|---|---|
| — | 0.9 | 0.05 | 0.4 | 0.02 | 0.08 | 0.12 | 0.08 | 0.05 | 0.03 | 0.2 |

TABLE III

POST-EMERGENCE TESTS
WEED SPECIES

| Cheatgrass | Crabgrass | Watergrass | Pigweed | Mustard | Fiddleneck |
|---|---|---|---|---|---|
| >5 | 0.9 | >5 | 0.44 | 0.28 | — |

The compound of the invention was tested in field tests as follows:

Test Series No. 1

Plots of ground commonly used for growing corn, in two locations in Illinois, were treated with the compound, at four dosage rates and by two modes of application: pre-planting incorporated (PPI) and pre-emergence (PE). The soil was heavy, having a relatively high (about 4 percent organic content. The tests were conducted in the period, April – June. The tests were for the purpose of determining whether the compound would control weeds commonly found in the area in which the tests were conducted, and the effect the compound might have upon crops (corn and soybeans) in the treated soil. In addition, seeds of annual ryegrass and redroot pigweed were broadcast over the test field areas, which then were harrowed. The compound was applied as a dilute aqueous suspension prepared by diluting with water an emulsible concentrate of the compound (12.5 percent) in a 50:50 mixture of cyclohexanone and xylene containing 5 percent emulsifier. The formulation was applied by a sprayer. Non-treated plots immediately adjacent to the treated plots served as controls. Irrigation was by natural rainfall.

PPI Tests

In these tests, the formulation of the compound was sprayed on the surface of the soil, which then was rototilled to mix the compound in the soil to a depth of about 3 inches. Seeds of the crop plants were then planted in the treated soil.

PE Tests

In these tests, the formulation of the compound was sprayed on the surface of the soil in which the seeds of the crop plants had already been planted.

Results

The effects of the compound on the corn plants were reported on the basis of visual assessment, in terms of a scale from 0 (no detectable effect) to 9 (no living tissue), with a rating of 3 (definite, but minor damage) being the maximum acceptable rating for a compound to be used for controlling weeds in the presence of seeds of plants of that particular crop. The effects of the compound on the weeds were reported as the percent control of the weeds, based on visual assessment and comparison to the weed growth in the control plots. To be useful as a practical herbicide, a compound must provide at least 70 – 80 percent control of the weeds. The results of these tests are reported in Table II.

PPI Tests

The compound was applied at dosages of 1.0, 0.5, 0.25 and 0.125 pound of compound per acre, at both locations.

At one location, neither compound gave any control of the weeds and had no effect on the crop plants.

At the other location, some control of weeds by the compound was obtained at a dosage of 1.0 pound per acre, while at other dosages, it had no effect. It caused minor damage to soybeans at 1.0 pounds per acre, but otherwise it had no effect on the crop plants. The control given by the compound at 1.0 pound per acre was as follows:

| Weed Species | Percent Control |
| --- | --- |
| Annual ryegrass | 80 |
| Giant foxtail | 90 |
| Velvet leaf | 30 |
| Pennsylvania smartweed | 90 |
| Prostrate pigweed | 30 |

TABLE II

| Plant Species | PRE-EMERGENCE Effect of Test Compound on Plants at Indicated Dosage[a] | | | | | | | |
| --- | --- | --- | --- | --- | --- | --- | --- | --- |
| | Test 1 | | | | Test 2 | | | |
| | 1.0 | 0.5 | 0.25 | 0.125 | 1.0 | 0.5 | 0.25 | 0.125 |
| Crops | | | | | | | | |
| Corn | 2 | * | * | *[b] | 0 | * | * | * |
| Soybean | 0 | * | * | * | 3 | * | * | * |
| Weeds | | | | | | | | |
| Annual Ryegrass | 70 | 50 | 0 | 0 | 60 | 50 | 0 | 0 |
| Giant Foxtail | 95 | 70 | 0 | 0 | 95 | 60 | 0 | 0 |
| Violet Leaf | 95 | 0 | 0 | 0 | 0 | 20 | 0 | 0 |
| Pennsylvania Smartweed | 90 | — | — | —[c] | 90 | 20 | 0 | 0 |
| Lambsquarters | 95 | 0 | 0 | 0 | — | — | — | — |
| Prostrate Pigweed | 99 | 0 | — | 0 | 90 | — | — | 0 |

[a]Pounds of test compound per acre.
[b]Asterisk indicates that the crop was not included in the particular test.
[c]Dash indicates that the weed was not in the particular plot involved.

Plots of ground commonly used for growing cotton, in Louisiana and Mississippi, were treated with the compound, at three dosage rates and by two modes of application: pre-planting incorporated (PPI) and pre-emergence (PE). The tests were conducted in the period, May – July. Tests 1 and 2 were conducted in Louisiana. Tests 3 and 4 were conducted in Mississippi. In both locations, the soil was light, having a relatively low (about 1 percent organic content. The tests were for the purpose of determining whether the compound would control weeds commonly found in the areas in which the tests were conducted, and the effect the compound might have upon crops (corn, cotton and soybeans) in the treated soil. The compound was applied as a dilute aqueous suspension prepared by diluting an emulsible concentrate of the compound with water. The dilute formulation was applied by a backpack sprayer. Non-treated plots immediately adjacent to the treated plots served as controls. Irrigation was by natural rainfall.

PPI Tests

In these tests, the formulation of the compound was sprayed on the surface of the soil, which then was cultivated with a DO-ALL soil bed conditioner (consisting of a non-powered rotary soil chopper, spike-tooth harrow and drag), which mixed the compound in the soil to a depth of about 3 inches. No weed seeds were planted — the soil was naturally infested with weed seeds. Seeds of the crop plants then were planted in the treated soil.

crop. The effects of the compound on the weeds were reported as the percent control of the weeds, based on visual assessment and comparison to the weed growth on the control plots. To be useful as a practical herbi-

TABLE III

PRE-PLANTING INCORPORATION
Effect of Test Compound on Plants at Indicated Dosage[a]

| Plant Species | Test 1 | | | Test 2 | | | Test 3 | | | Test 4 | | |
|---|---|---|---|---|---|---|---|---|---|---|---|---|
| | 1.0[a] | 0.5 | 0.25 | 1.0 | 0.5 | 0.25 | 1.0 | 0.5 | 0.25 | 1.0 | 0.5 | 0.25 |
| Crops | | | | | | | | | | | | |
| Corn | 2 | 0 | 0 | 2 | 0 | 0 | 0 | 0 | 0 | 0 | 0 | 0 |
| Cotton | 3 | 0 | 0 | 0 | 0 | 0 | 0 | 0 | 0 | 0 | 0 | 0 |
| Soybean | 9 | 6 | 5 | 6 | 4 | 0 | 4 | 0 | 0 | 0 | 0 | * |
| Weeds | | | | | | | | | | | | |
| Pigweed | 80 | 30 | 0 | 80 | 40 | 0 | 100 | 90 | 0 | 90 | 0 | 0 |
| Goosegrass | 90 | 60 | 0 | 75 | 70 | 0 | 100 | 100 | 0 | 80 | 40 | 0 |
| Johnsongrass | 0 | 0 | 0 | — | — | — | — | — | 0 | 80 | 0 | 0 |
| Morninglory | 80 | 0 | 0 | 20 | 0 | 0 | — | — | — | 0 | 0 | 0 |
| Signalgrass | 30 | 0 | 0 | 60 | — | 0 | — | — | 0 | — | — | — |
| Sida | 100 | — | — | — | — | — | 90 | 0 | 0 | — | — | 0 |
| Carpetweed | 90 | 50 | 0 | 100 | 90 | — | — | — | — | — | — | — |
| Spurge | — | — | — | — | — | — | 90 | 90 | 0 | 80 | 40 | 0 |
| Copperleaf | — | — | — | — | — | — | — | — | — | 90 | 0 | — |

[a] Pounds of test compound per acre.
[b] Dash indicates that the weed was not found in the particular plot involved.
[c] Asterisk indicates that soybeans were not included in the particular test.

TABLE IV

PRE-PLANTING INCORPORATION
Effect of Test Compound of Plants at Indicated Dosage[a]

| Plant Species | Test 1 | | | Test 2 | | | Test 3 | | | Test 4 | | |
|---|---|---|---|---|---|---|---|---|---|---|---|---|
| | 1.0 | 0.5 | 0.25 | 1.0 | 0.5 | 0.25 | 1.0 | 0.5 | 0.25 | 1.0 | 0.5 | 0.25 |
| Crops | | | | | | | | | | | | |
| Corn | 5 | 4 | 0 | 3 | 0 | 0 | 2 | 1 | 0 | 3 | 0 | 0 |
| Cotton | 3 | 0 | 0 | 0 | 4 | 0 | 0 | 0 | 0 | 0 | 0 | 0 |
| Soybean | 8 | 4 | 0 | 8 | 7 | 0 | 9 | 7 | 7 | 6 | 6 | 6 |
| Weeds | | | | | | | | | | | | |
| Pigweed | 100 | 90 | 80 | 100 | 100 | 50 | 100 | 40 | 0 | 100 | — | 0 |
| Goosegrass | 100 | 100 | 80 | 95 | 90 | 70 | 100 | 80 | — | 95 | 95 | 0 |
| Johnsongrass | — | 0 | — | — | 50 | 0 | 0 | 0 | 0 | — | 0 | 0 |
| Morninglory | 0 | 0 | 0 | 70 | 0 | 0 | 0 | 0 | 0 | — | 0 | 0 |
| Signalgrass | 100 | — | — | 90 | 0 | 0 | — | — | — | — | — | — |
| Sida | — | — | — | — | — | — | — | — | — | — | — | 0 |
| Carpetweed | 100 | 90 | 80 | 50 | 50 | 0 | — | — | — | — | — | — |
| Spurge | — | — | — | — | — | 0 | 100 | 90 | 50 | 95 | 60 | 0 |
| Copperleaf | — | 90 | 50 | — | — | 0 | 100 | — | — | 90 | — | — |

[a] Pounds of test compound per acre.
[b] Dash indicates that the weed was not found in the particular plot involved.
[c] Asterisk indicates that soybeans were not included in the particular test.

PE Tests

In these tests, the formulation of the compound was sprayed on the surface of the soil, in which the seeds of the crop plants had already been planted.

Results

The results of the tests are summarized in Tables III – IV. The effects of the test compound on the crop plants were reported on the basis of visual assessment, in terms of a scale from 0 (no detectable effect) to 9 (no living tissue), with a rating of 3 (definite, but minor damage) being the maximum acceptable rating for a compound to be able to be used for controlling weeds in the presence of seeds of plants of that particular crop. The effects of the compound on the weeds were reported as the percent control of the weeds, based on visual assessment and comparison to the weed growth on the control plots. To be useful as a practical herbicide, a compound must provide at least 70–80 percent control of the weeds.

What is claimed is:
1. 1-methoxy-1-methyl-3-(3-perchlorylphenyl)-urea.
2. A herbicidal composition comprising an effective amount of the compound of claim 1 together with an inert adjuvant therefor.
3. A method for controlling unwanted plants which comprises subjecting such plants to an effective dosage of the compound of claim 1.
4. A method for controlling unwanted plants which comprises applying to the soil in which seeds of such plants are present an effective dosage of the compound of claim 1.

* * * * *